US008545865B2

(12) United States Patent
Boden

(10) Patent No.: US 8,545,865 B2
(45) Date of Patent: Oct. 1, 2013

(54) MEDICAL DEVICES HAVING POLYMER BRUSHES

(75) Inventor: Mark Boden, Harrisville, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1906 days.

(21) Appl. No.: 11/388,652

(22) Filed: Mar. 24, 2006

(65) Prior Publication Data

US 2007/0224236 A1 Sep. 27, 2007

(51) Int. Cl.
*A61F 2/00* (2006.01)
(52) U.S. Cl.
USPC ............................ 424/423; 424/422; 623/1.15
(58) Field of Classification Search
USPC .......................... 424/422, 423, 424, 425, 426
See application file for complete search history.

(56) References Cited

U.S. PATENT DOCUMENTS

| | | | | |
|---|---|---|---|---|
| 6,150,459 | A * | 11/2000 | Mayes et al. | 525/54.1 |
| 6,545,097 | B2 | 4/2003 | Pinchuk et al. | 525/240 |
| 2002/0128234 | A1* | 9/2002 | Hubbell et al. | 514/100 |
| 2003/0219535 | A1 | 11/2003 | Chang et al. | 427/255.6 |
| 2003/0236323 | A1 | 12/2003 | Ratner | 524/27 |
| 2003/0236513 | A1 | 12/2003 | Schwarz et al. | 604/890.1 |
| 2003/0236514 | A1 | 12/2003 | Schwarz | 604/890.1 |
| 2004/0185260 | A1* | 9/2004 | Luzinov et al. | 428/413 |
| 2005/0002865 | A1 | 1/2005 | Klaveness et al. | 424/9.52 |
| 2005/0025802 | A1 | 2/2005 | Richard et al. | 424/423 |
| 2005/0171596 | A1 | 8/2005 | Furst et al. | 623/1.15 |
| 2005/0187146 | A1 | 8/2005 | Helmus et al. | 514/8 |
| 2006/0009550 | A1* | 1/2006 | Messersmith et al. | 524/17 |
| 2006/0013853 | A1 | 1/2006 | Richard | 424/423 |

FOREIGN PATENT DOCUMENTS

| | | |
|---|---|---|
| EP | 1 754 731 A1 | 2/2007 |
| WO | WO 2004/090004 A1 | 10/2004 |

OTHER PUBLICATIONS

"Functionalization of Polymer Surfaces," Europlasma Technical Paper, May 8, 2004, 29 pp.
M. Claes et al., "Polymer Coating of Steel by a Combination of Electrografting and Atom-Transfer Radical Polymerization," *Macromolecules*, vol. 36 (2003): 5926-5933.
Jeffrey Pyun et al., "Synthesis of Nanocomposite Organic/Inorganic Hybrid Materials Using Controlled/"Living " Radical Polymerization," *Chem. Mater.*, vol. 13 (2001): 3436-3448.
Denys Usov et al., "Mixed Polymer Brushes with Thermal Response Amplified by Roughness," *Polymeric Materials: Science & Engineering*, vol. 90 (2004): 622-623.
Mikhail Motornov et al., "Mixed polymer brushes on polyamide substrates," *Polymeric Materials: Science & Engineering*, vol. 88 (2003): 264-265.
Igor Luzinov et al., "Hybrid Polymer Nanolayers for Surface Modification of Fibers," National Textile Center Annual Report: Nov. 2004, 10 pp.
Victor Klep et al., "Mixed Polymer Layers by 'Grafting to'/'Grafting from' Combination," *Polymeric Materials: Science & Engineering*, vol. 89 (2003): 248-249.
S.A. Prokhorova et al., "Can polymer brushes induce motion of nano-objects?" *Nanotechnology*, vol. 14 (2003): 1098-1108.
Liming Dai et al., "Functionalized surfaces based on polymers and carbon nanotubes for some biomedical and optoelectronic applications," *Nanotechnology*, vol. 14 (2003): 1081-1097.
Polymer Brushes. http://www.2.uakron.edu/cpspe/DPS/fachome/WJB/research/Polymer%20Brush%20Summary.html. Mar. 28, 2006 download. 3 pp.
Svetlana Santer et al., "Motion of nano-objects on polymer brushes," Polymer, vol. 45 (2004): 8279-8297.
Responsive Polymer Brushes. http://people.clarkson.edu/~sminko/nanostructured/responsive-smar-materials/responsive-polymer . . . Mar. 30, 2005 download, 1 p.
Alexander Sidorenko et al., "Switching of Polymer Brushes," *Langmuir*, vol. 15 (1999): 8349-8355.
Petra Uhlmann et al., Surface functionalization by smart binary polymer brushes to tune physiko-chemical characteristics at biointerfaces. http://www.science24.com/paper/1847. Mar. 19, 2006 download. 1 p.
Petra Uhlman et al., Surface functionalization by Smart Coatings: Stimuli-responsive binary polymer brushes. http://www.coatings-science.chem.tue.nl/speakers/Uhlman.html. Mar. 19, 2006 download. 1 p.
D. Usov et al. Observation of microphase segregation in binary polymer brushes. http://www-als.lbl.gov/als/compendium/AbstractManager/uploads/01036.pdf. Advanced Light Source, Compendium of User Abstracts 2001, 1 p.
S. Minko et al., "Lateral versus Perpendicular Segregation in Mixed Polymer Brushes," *Physical Review Brushes*, vol. 88 (2002): 035502-1-035502-4.
Carnegie Mellon, The Matyjaszewski Polymer Group. Research Areas. http://www.chem.cmu.edu/groups/maty/about/research/about-research-hybrid.html. Mar. 19, 2006 download. 8 pp.
Sergiy Minko et al., Synthesis of Binary Polymer Brushes Via 'Grafting to' Approach, *Polymeric Materials: Science & Engineering*, vol. 84 (2001): 877-878.

* cited by examiner

*Primary Examiner* — James Rogers
(74) *Attorney, Agent, or Firm* — Mayer & Williams PC; David B. Bonham

(57) ABSTRACT

According to an aspect of the present invention, internal medical devices are provided, which contain at least one surface region that comprises a polymer brush. The polymer brush, in turn, contains one or more types of hydrophobic polymer chains and one or more types of hydrophilic polymer chains.

18 Claims, No Drawings

MEDICAL DEVICES HAVING POLYMER BRUSHES

FIELD OF THE INVENTION

The present invention relates to medical devices and more particularly to medical devices having polymer brushes that change properties upon implantation or insertion of the devices into patients.

BACKGROUND OF THE INVENTION

Surface properties of medical devices touch upon a whole host of issues, including mechanical performance and biocompatibility, among many others. For example, during a typical balloon angioplasty procedure, a stent is crimped upon a balloon and advanced into the vasculature of a patient. The stent is subsequently expanded upon balloon inflation to engage the walls of a blood vessel, thereby providing patency to the vessel. In general, the lower the surface energy of the stent, the greater the ease of balloon withdrawal after the stent is expanded. Because they are hydrophobic, however, devices having low surface energies are not necessarily desirable from a biocompatibility standpoint.

The in vivo delivery of a biologically active agent within the body of a patient is common in the practice of modern medicine. In vivo delivery of biologically active agents is often implemented using medical devices that may be temporarily or permanently placed at a target site within the body. These medical devices can be maintained, as required, at their target sites for short or prolonged periods of time, delivering biologically active agents at the target site. For example, drug delivery from stents for the treatment of restenosis is widely accepted. Commercially available drug eluting coronary stents include those available from Boston Scientific Corp. (TAXUS), Johnson & Johnson (CYPHER), and others. Unfortunately, only a few products have been successful to date, in part, due to the inability to create products with effective and safe dose and release kinetics. For coronary stents with polymeric drug-eluting coatings, dose and release kinetics may be affected, for example, by the physiochemical properties of the drug and the polymeric carrier, by the interactions between the drug and carrier, and by the geometry of the system.

SUMMARY OF THE INVENTION

According to an aspect of the present invention, internal medical devices are provided, which contain at least one surface region that comprises a polymer brush. The polymer brush, in turn, contains one or more types of hydrophobic polymer chains and one or more types of hydrophilic polymer chains.

An advantage of the present invention is that internal medical devices are provided, which change properties upon introduction into a patient.

These and other aspects, embodiments and advantages of the present invention will become immediately apparent to those of ordinary skill in the art upon review of the Detailed Description and Claims to follow.

DETAILED DESCRIPTION OF THE INVENTION

As is well known, "polymers" are molecules that contain multiple copies of the same or differing constitutional units, commonly referred to as monomers. The number of constitutional units within a given polymer may vary widely, ranging, for example, from 5 to 10 to 25 to 50 to 100 to 1000 to 10,000 or more constitutional units. Polymers for use in the present invention may have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains) and dendritic architectures (e.g., arborescent and hyperbranched polymers), among others. The polymers may contain, for example, homopolymer chains, which contain multiple copies of a single constitutional unit, and/or copolymer chains, which contain multiple copies of at least two dissimilar constitutional units, which units may be present in any of a variety of distributions including random, statistical, gradient, and periodic (e.g., alternating) distributions. As defined herein, "block copolymers" are polymers containing two or more differing polymer chains with covalent linkages, for example, selected from homopolymer chains and copolymer chains (e.g., random, statistical, gradient, and periodic copolymer chains).

According to an aspect of the invention, internal medical devices (i.e., medical devices that are adapted for implantation or insertion into a patient) are provided, which comprise polymer brushes at their surfaces. In some embodiments of the present invention, therapeutic agents are disposed within or beneath the polymer brushes. Typical subjects (or "patients") are vertebrate subjects, more typically mammalian subjects, and even more typically human subjects.

"Polymer brushes," as the name suggests, contain polymer chains, one end of which is directly or indirectly tethered to a surface and another end of which is free to extend from the surface, somewhat analogous to the bristles of a brush. In the devices of the present invention, polymer brushes are employed, which have one or more types of hydrophobic polymer chains and one or more types of hydrophilic polymer chains. These incompatible polymer chains are capable of phase separating into distinct phase domains, one type of which preferentially orients at the surface, depending on nature of the surrounding environment. This process is sometimes called perpendicular segregation. For example, upon exposure to a hydrophobic environment (e.g., exposure to a relatively nonpolar organic solvent such as toluene), the surface becomes more hydrophobic due to the migration of the hydrophobic chains to the surface and the formation of a hydrophobic phase domain (e.g., a continuous or discontinuous phase domain) there, whereas upon exposure to a hydrophilic environment (e.g., exposure to an aqueous environment or exposure to a relatively polar organic solvent such as methanol or ethanol), the surface becomes more hydrophobic because the hydrophobic chains migrate to the surface forming a surface a hydrophilic phase domain. As a result of this ability to change properties, such polymer brushes are sometimes referred to a stimulus responsive, "switchable" or "smart".

As used herein, "polymer brush regions" are surface regions having polymer brushes.

Typically, stimulus responsive polymer brushes fall into one of two categories. In the first category, one or more types of hydrophobic chains and one or more types of hydrophilic chains extend separately from the surface. In the second category, one or more hydrophobic chains and one or more hydrophilic chains are provided within a single block copolymer that extends from the surface.

A variety of internal medical devices and portions thereof may be provided with polymer brush regions including, for example, catheters (e.g., renal or vascular catheters), balloons, catheter shafts, guide wires, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, vascular valves, tissue engineering scaffolds for cartilage, bone, skin and other in vivo tissue regeneration, and so forth.

The polymer brushes may be provided over the entire surface of the medical device or over only a portion of the medical device surface. For example, with tubular devices such as stents (which can comprise, for example, a laser or mechanically cut tube, or one or more braided, woven, or knitted filaments, etc.), polymer brushes may be provided over the entire surface of the stent, or they may be provided on the inner luminal surface of the stent, on the outer abluminal surface of the stent, and/or on the lateral surfaces between the luminal and abluminal surfaces (including the ends). The polymer brushes may be provided in desired patterns, for instance, using appropriate masking techniques. As another example, polymer brushes may be provided over some device components but not others (e.g., over the balloon of a balloon catheter, but not over the catheter shaft).

A few exemplary uses for medical devices in accordance with the invention will now be discussed. As a first example, it is known that adhesion between a balloon and surrounding stent can lead to an increase in the force that is needed for balloon withdrawal. It is also known that materials having low surface energy, including a wide variety of homopolymer and copolymer chains, are hydrophobic and that they typically exhibit low frictional forces when moved along the surface of another material. By providing a medical device with a polymer brush region in accordance with the invention and by ensuring that the coated device is exposed to a hydrophobic environment prior to delivery to a patient, the hydrophobic polymer component is segregated at the surface, thereby giving the overall device a low surface energy. For example, by soaking the device in a solvent which is selective for the hydrophobic chains and flash drying to remove the solvent, a coating may be provided whose surface is primarily composed of hydrophobic polymer chains. Where the device is a stent, the resulting hydrophobic surface may facilitate withdrawal of the balloon, after which the surface becomes hydrophilic in the aqueous environment of the body.

The wide range of choices for the hydrophobic chains will enable tailoring the surface properties of the device, including surface energy and hardness, among others. In the case of a stent, this may allow the frictional forces to the varied, for example, allowing the optimization of both the securement and withdrawal of the stent.

An advantage of a brush polymer surface having both hydrophilic and hydrophobic polymer chains is that the surface will reorient once it is exposed to an aqueous environment, resulting in a surface that is primarily composed of hydrophilic chains such that a hydrophilic surface is presented to the surrounding environment. Therefore, the device biocompatibility will actually change after the device is deployed. Selection of the proper hydrophilic polymer chains will allow control of the compatibility. As discussed further below, rigidity is related to the glass transition temperature of the polymer chains, with high glass transition temperature chains being more rigid and low glass transition temperature chains being more flexible.

In this manner, two polymer chains may be selected—one that is optimized for balloon adhesion and release, and another that is optimized for biocompatibility. Examples of hydrophobic polymer chains include those that are glassy or partially crystalline at the application temperature, for instance, polystyrene and its derivatives, polyacrylates having alkyl side chains, and so forth. Examples of hydrophobic polymer chains also include those that are soft at the application temperature, for instance, polyalkylene chains, poly(halogenated alkylene) chains and polysiloxane chains. Examples of hydrophilic polymer chains include materials such as peptides or their synthetic derivatives, polyalkylene oxides (e.g., PEO), ionic polymers including polyelectrolytes, and so forth. For example, use of poly(methyl methacrylate) chains will result in a relatively rigid surface that may adsorb biopolymers, whereas use of glycol ether chains will result in a softer segment that may prevent biofouling and impart completely different properties to the device surface. In addition, the hydrophilic polymer chain may be formed from a bioactive polymer, thereby promoting healing, preventing thrombolytic reactions, or serving as a binding site for antibodies, cells, and so forth. Further hydrophobic and hydrophilic chains may be selected from those set forth below.

Polymer brush regions may be provided over a number of medical device substrates. Materials for use as underlying medical device substrates include (a) organic materials (e.g., materials containing 50 wt % or more organic species) such as polymeric materials and (b) inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals (e.g., biostable metals such as gold, platinum, palladium, iridium, osmium, rhodium, titanium, tantalum, tungsten, and ruthenium, and bioresorbable metals such as magnesium) and metal alloys, including metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), and alloys comprising nickel and chromium (e.g., inconel alloys).

Specific examples of organic materials may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-alkylene copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as further copolymers and blends of the above.

Where implantable or insertable medical devices are provided which contain polymer brush regions that regulate the release of therapeutic agents, the release profile associated with such devices may be modified, for example, by changing the chemical composition, size, and/or number of the polymer brush regions on the device, among other parameters. For example, the release profile may be affected by the concentration of therapeutic agent(s) within the polymer brush region(s), by the polymer composition of the polymer brush region(s), by the surface area of the polymer brush region(s), and so forth. Multiple polymer brush region(s), having either the same content or different content (e.g., different polymer and/or therapeutic agent content), may be provided on the medical device surfaces. Hence, polymer brush region(s) may be adapted to release the same or different therapeutic agents, at the same or different rates, from different locations on the medical device. For instance, a tubular medical device (e.g., a vascular stent) may be provided which has a polymer brush region that contains or is disposed over an antithrombotic agent at its inner, luminal surface and a second polymer brush region which contains or is disposed over therapeutic agents at its outer, abluminal surface (as well as on the ends, if desired).

As indicated above, delivery of a therapeutic agent may be modified by varying the brush materials that are utilized. For instance, a drug may be added that is preferentially associated with either of the hydrophilic or the hydrophobic phase domains (e.g., because it is soluble in or otherwise compatible with either of the phase domains). If the drug is associated with the more hydrophobic phase domain that is initially oriented at the surface, the drug may be relatively rapidly released, for example, in a burst process. If the drug is instead associated with the more hydrophilic domain phase domain, it may elute primarily after the surface has reoriented at the site of use.

More specifically, a hydrophobic drug that is associated with the hydrophobic domain is initially exposed at the surface of the device, and is subsequently internalized as the brushes reoriented to present a hydrophilic surface. The overall result may be an initial burst of drug, followed by a slow release over time, as the drug diffuses through the hydrophilic surface to elute. Conversely, if the drug is associated with the hydrophilic domain, there may be little or no initial release. However, as the surface reorients itself, the release drug may increase. The overall result in this case may be an initial period of little or no drug release, followed by fairly rapid, diffusion controlled release.

The polymer brush region may also serve to regulate delivery of a drug primarily residing in the substrate on which the polymer brush is prepared (e.g., within a polymer coating that the brush is prepared upon). In this case, the rate of release of the drug may depend, for example, on the relative amounts of each phase domain and the relative solubility of the drug within each phase domain. For instance, in the event that the hydrophobic phase domain oriented at the surface is incompatible with the drug, it essentially forms a barrier layer initially. As the two polymers phases start to reorient such that the hydrophilic polymer phase is preferentially at the surface, conduit for drug release may be formed allowing the release rate to increase. Conversely, if the hydrophobic phase initially oriented at the surface is compatible with the drug, release should be rapid, followed by a decrease in release rate as the two polymer chains/phase reorient and the non-solvent polymer eventually forms a barrier layer at the surface.

A wide range of polymers is available for forming the polymer chains of polymer brushes, specific examples of which may be selected, for example, from the polymers listed above for use in substrates.

The hydrophobic and hydrophilic polymer chains within the polymer brushes may be, for example, either high $T_g$ or low $T_g$ polymer chains. In general, low $T_g$ polymer chains are soft and elastomeric at room (and body) temperature, whereas high $T_g$ polymer chains are hard. In certain advantageous embodiments of the invention, the hydrophobic polymer chains within the polymer brush are high $T_g$ polymer chains (e.g., to reduce surface tack), whereas the hydrophilic polymer chains may be high $T_g$ polymer chains or low $T_g$ polymer chains. Where the hydrophobic and hydrophilic polymer chains are both high $T_g$ polymer chains, the switching time for the polymers may be increase, due to the rigidity of the polymer chains.

As used herein, "low $T_g$ polymer chains" are those that display a $T_g$ that is below body temperature, more typically 37° C. to 20° C. to 0° C. to −25° C. to −50° C. or below. Conversely, elevated or "high $T_g$ polymer chains" are those that display a glass transition temperature that is above body temperature, more typically 37° C. to 50° C. to 75° C. to 100° C. or above. $T_g$ can be measured by any of a number of techniques including differential scanning calorimetry (DSC), dynamic mechanical analysis (DMA), or dielectric analysis (DEA). It may be possible to measure $T_g$ for polymer brushes directly, for example, using selective surface probe microscope or atomic force microscope techniques. Alternatively, $T_g$ may be determined for the polymer chains when in free form (i.e., when not tethered to the surface).

In cases where the hydrophilic and hydrophobic polymer chains are present within a single block copolymer, configurations may vary widely. Examples include the following:

$CB_HL_H$, $CL_HB_H$, $B_HCL_H$, $L_HCB_H$, $CB_HL_L$, $CL_LB_H$, $B_HCL_L$, $L_LCB_H$, $CB_LL_H$, $CL_HB_L$, $B_LCL_H$, $L_HCB_L$, $CB_LL_L$, $CL_LB_L$, $B_LCL_L$, $L_LCB_L$, where C is a covalent linking entity for linkage to the substrate surface, $B_H$ is a hydrophobic high $T_g$ chain, $B_L$ is a hydrophobic low $T_g$ chain, $L_H$ is a hydrophilic, high $T_g$ chain, and $L_L$ is a hydrophilic, low $T_g$ chain.

Of course other block copolymer configurations may be employed, for example, copolymers which contain a main chain (which may be, for example, hydrophobic, hydrophilic or amphiphilic, low or high $T_g$) from which extends a mixture of hydrophilic (low or high $T_g$) and hydrophobic (low or high $T_g$) side chains, among many other possibilities.

Alternatively, the block copolymer may be linked to the substrate by non-covalent interactions. Examples include the following $PB_HL_H$, $PB_HL_L$, $PL_HB_H$, $PL_LB_H$, $B_HPL_H$, $B_HPL_L$, $L_HPB_H$, $L_LPB_H$, $PB_LL_H$, $PB_LL_L$, $PL_HB_L$, $PL_LB_L$, $B_LPL_H$, $B_LPL_L$, $L_HPB_L$, and $L_LPB_L$ where P is a polymeric chain which is capable of adsorption on the substrate. Note that the hydrophilic (low or high $T_g$) and hydrophobic (low or high $T_g$) may be provided, for example, at opposite ends of the polymer chain P, along the backbone of the polymer chain P, and so forth.

Examples of low $T_g$ chains include low $T_g$ polyalkylene chains, low $T_g$ polysiloxane chains, low $T_g$ poly(halogenated alkylene) chains, low $T_g$ polyacrylate chains, low $T_g$ polymethacrylate chains, low $T_g$ poly(vinyl ether) chains, and low $T_g$ poly(cyclic ether) chains, among others.

Examples of high $T_g$ chains include vinyl aromatic chains, such as those made from styrenic monomers, high $T_g$ poly-acrylate chains, high $T_g$ polymethacrylate chains, poly(vinyl alcohol) chains, high $T_g$ poly(vinyl ester) chains, high $T_g$ poly(vinyl amine) chains, high $T_g$ poly(vinyl halide) chains, high $T_g$ poly(alkyl vinyl ethers), and high $T_g$ polyamide chains, among others.

Specific examples of low $T_g$ polymer chains include those that consist of or contain one or more monomers selected from the following (listed along with published $T_g$'s for homopolymers of the same): (1) acrylic monomers including: (a) alkyl acrylates such as methyl acrylate ($T_g$ 10° C.), ethyl acrylate ($T_g$-24° C.), propyl acrylate, isopropyl acrylate ($T_g$-11° C., isotactic), butyl acrylate ($T_g$-54° C.), sec-butyl acrylate ($T_g$-26° C.), isobutyl acrylate ($T_g$-24° C.), cyclohexyl acrylate ($T_g$ 19° C.), 2-ethylhexyl acrylate ($T_g$-50° C.), dodecyl acrylate ($T_g$-3° C.) and hexadecyl acrylate ($T_g$ 35° C.), (b) arylalkyl acrylates such as benzyl acrylate ($T_g$ 6° C.), (c) alkoxyalkyl acrylates such as 2-ethoxyethyl acrylate ($T_g$-50° C.) and 2-methoxyethyl acrylate ($T_g$-50° C.), (d) halo-alkyl acrylates such as 2,2,2-trifluoroethyl acrylate ($T_g$-10° C.) and (e) cyano-alkyl acrylates such as 2-cyanoethyl acrylate ($T_g$ 4° C.); (2) methacrylic monomers including (a) alkyl methacrylates such as butyl methacrylate ($T_g$ 20° C.), hexyl methacrylate ($T_g$-5° C.), 2-ethylhexyl methacrylate ($T_g$-10° C.), octyl methacrylate ($T_g$-20° C.), dodecyl methacrylate ($T_g$-65° C.), hexadecyl methacrylate ($T_g$ 15° C.) and octadecyl methacrylate ($T_g$-100° C.) and (b) aminoalkyl methacrylates such as diethylaminoethyl methacrylate ($T_g$ 20° C.) and 2-tert-butyl-aminoethyl methacrylate ($T_g$ 33° C.); (3) vinyl ether monomers including (a) alkyl vinyl ethers such as ethyl vinyl ether ($T_g$-43° C.), propyl vinyl ether ($T_g$-49° C.), butyl vinyl ether ($T_g$-55° C.), isobutyl vinyl ether ($T_g$-19° C.), 2-ethylhexyl vinyl ether ($T_g$-66° C.) and dodecyl vinyl ether ($T_g$-62° C.); (4) cyclic ether monomers include tetrahydrofuran ($T_g$-84° C.), trimethylene oxide ($T_g$-78° C.), ethylene oxide ($T_g$-66° C.), propylene oxide ($T_g$-75° C.), methyl glycidyl ether ($T_g$-62° C.), butyl glycidyl ether ($T_g$-79° C.), allyl glycidyl ether ($T_g$-78° C.), epibromohydrin ($T_g$-14° C.), epichlorohydrin ($T_g$-22° C.), 1,2-epoxybutane ($T_g$-70° C.), 1,2-epoxyoctane ($T_g$-67° C.) and 1,2-epoxydecane ($T_g$-70° C.); (5) ester monomers (other than acrylates and methacrylates) including ethylene malonate ($T_g$-29° C.), vinyl acetate ($T_g$ 30° C.), and vinyl propionate ($T_g$ 10° C.); (6) alkene monomers including ethylene, propylene ($T_g$-8 to -13° C.), isobutylene ($T_g$-73° C.), 1-butene ($T_g$-24° C.), trans-butadiene ($T_g$-58° C.), 4-methyl pentene ($T_g$ 29° C.), 1-octene ($T_g$-63° C.) and other α-olefins, cis-isoprene ($T_g$-63° C.), and trans-isoprene ($T_g$-66° C.); (7) halogenated alkene monomers including vinylidene chloride ($T_g$-18° C.), vinylidene fluoride ($T_g$-40° C.), cis-chlorobutadiene ($T_g$-20° C.), and trans-chlorobutadiene ($T_g$-40° C.); and (8) siloxane monomers including dimethylsiloxane ($T_g$-127° C.), diethylsiloxane, methylethylsiloxane, methylphenylsiloxane ($T_g$-86° C.), and diphenylsiloxane.

Specific examples of high $T_g$ polymer chains further include those that consist of or contain one or more monomers selected from the following: (1) vinyl aromatic monomers including (a) unsubstituted vinyl aromatics, such as styrene ($T_g$ 100° C.) and 2-vinyl naphthalene ($T_g$ 151° C.), (b) vinyl substituted aromatics such as a-methyl styrene, and (c) ring-substituted vinyl aromatics including ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), ring-alkoxylated vinyl aromatics, such as 4-methoxystyrene ($T_g$ 113° C.) and 4-ethoxystyrene ($T_g$ 86° C.), ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 118° C.) and 4-fluorostyrene ($T_g$ 95° C.) and ring-ester-substituted vinyl aromatics such as 4-acetoxystyrene ($T_g$ 116° C.); (2) other vinyl monomers including (a) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (b) vinyl amines such as 2-vinyl pyridine ($T_g$ 104° C.), 4-vinyl pyridine ($T_g$ 142° C.), and vinyl carbazole ($T_g$ 227° C.), (c) vinyl halides such as vinyl chloride ($T_g$ 81° C.) and vinyl fluoride ($T_g$ 40° C.); (d) alkyl vinyl ethers such as tert-butyl vinyl ether ($T_g$ 88° C.) and cyclohexyl vinyl ether ($T_g$ 81° C.), and (e) other vinyl compounds such as vinyl ferrocene ($T_g$ 189° C.); (3) other aromatic monomers including acenaphthalene ($T_g$ 214° C.) and indene ($T_g$ 85° C.); (4) methacrylic monomers including (a) methacrylic acid anhydride ($T_g$ 159° C.), (b) methacrylic acid esters (methacrylates) including (i) alkyl methacrylates such as atactic methyl methacrylate ($T_g$ 105-120° C.), syndiotactic methyl methacrylate ($T_g$ 115° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (c) other methacrylic-acid derivatives including methacrylonitrile ($T_g$ 120° C.); (5) acrylic monomers including (a) certain acrylic acid esters such as tert-butyl acrylate ($T_g$ 43-107° C.), hexyl acrylate ($T_g$ 57° C.) and isobornyl acrylate ($T_g$ 94° C.); and (b) other acrylic-acid derivatives including acrylonitrile ($T_g$ 125° C.). Further specific examples of high $T_g$ polymer chains include polyamide chains selected from nylon homopolymer and copolymer chains such as nylon 6, nylon 4/6, nylon 6/6, nylon 6/10, nylon 6/12, nylon 11 and nylon 12 chains.

Further specific examples of high and low $T_g$ polymer chains include polymer chains that consist of or contain one or more monomers selected from the following: (a) polyester-forming monomers such as naphthalate and terephthalate esters (the $T_g$ is 70-80° C. for polyethylene terephthalate), d-lactide, 1-lactide ($T_g$ 60-65° C.), glycolic acid ($T_g$ 35-40° C.), epsilon-caprolactone ($T_g$-65 to -60° C.), hydroxybutyrate, and hydroxyvalerate, (b) monomers that form polyether-esters such as p-dioxanone ($T_g$-10 to 0° C.), and (c) monomers that form polycarbonates such as ethylene carbonate (1,3-dioxolan-2-one) ($T_g$ 10 to 30° C.), propylene carbonate (4-methyl-1,3-dioxolan-2-one), trimethylene carbonate (1,3-dioxan-2-one), tetramethylene carbonate (1,3-dioxepan-2-one), as well as 1,4-dioxepan-2-one, 1,5-dioxepan-2-one and 6,6-dimethyl-1,4-dioxan-2-one.

Further examples of hydrophobic and hydrophilic polymer chains (which may be high or low $T_g$ polymer chains), include hydrophobic and hydrophilic biodegradable chains such as those listed in the prior paragraph as well as hydrophobic and hydrophilic bioactive polymer chains and hydrophobic and hydrophilic biomimetic polymer chains.

For example, hydrophobic and hydrophilic polymer chains may be selected from one or more of the following (predominantly hydrophilic) chains: the subunit chains found in collagen, laminin or fibronectin, elastin chains, polymer chains containing cell adhesion peptides such as RGD tripeptide (i.e., ArgGlyAsp), REDV tetrapeptide (i.e., Arg—Glu—Asp—Val), and YIGSR pentapeptide (i.e., TyrIleGlySerArg), glycoprotein chains, polyanhydride chains, polyorthoester chains, polyphosphazene chains, and sulfated and non-sulfated polysaccharide chains, such as chitin, chitosan, sulfated and non-sulfated glycosaminoglycans as well as species containing the same such as proteoglycans, for instance, selected from heparin, heparin sulfate, chondroitin sulfates including chondroitin-4-sulfate and chondroitin-6-sulfate, hyaluronic acid, keratan sulfate, dermatan sulfate, hyaluronan, bamacan, perlecan, biglycan, fibromodulin, aggrecan, decorin, mucin, carrageenan, polymers and copolymers of uronic acids such as mannuronic acid, galatcuronic acid and guluronic acid, for example, alginic acid (a copolymer of beta-D-mannuronic acid and alpha-L-guluronic acid), which charged polysaccharide species may be attached to a cell adhesion peptide, a protein, a protein fragment and/or a biocompatible polymer, as described in U.S. Pat. App. No. 2005/0187146 to Helmus et al.

As noted above, the medical devices of the present invention optionally contain one or more therapeutic agents. "Therapeutic agents," "drugs," "pharmaceutically active agents," "pharmaceutically active materials," and other related terms may be used interchangeably herein. These terms include genetic therapeutic agents, non-genetic therapeutic agents and cells.

Therapeutic agents include, for example, adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiuretics, antidotes, antidyskinetics agents, anti-emetic agents, anti-epileptic agents, anti-estrogen agents, antifibrinolytic agents, antifungal agents, antiglaucoma agents, antihemophilic agents, antihemophilic Factor, antihemorrhagic agents, antihistaminic agents, antihyperlipidemic agents, antihyperlipoproteinemic agents, antihypertensives, antihypotensives, anti-infective agents, anti-inflammatory agents, antikeratinizing agents, antimicrobial agents, antimigraine agents, antimitotic agents, antimycotic agents, antineoplastic agents, anti-cancer supplementary potentiating agents, antineutropenic agents, antiobsessional agents, antiparasitic agents, antiparkinsonian drugs, antpneumocystic agents, antiproliferative agents, antiprostatic hypertrophy drugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immunostimulants, immunosuppressants, impotence therapy adjuncts, keratolytic agents, LHRH agonists, luteolysin agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine Al antagonists, serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like.

Further examples of therapeutic agents useful for the practice of the present invention may be selected, for example, from those described in paragraphs [0040] to of commonly assigned U.S. Patent Application Pub. No. 2003/0236514, the disclosure of which is hereby incorporated by reference.

Additional specific examples may be selected, for example, from paclitaxel (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), heparin, as well a derivatives of the forgoing, among others.

Polymer brush regions may be created by various methods, including covalent and non-covalent (e.g., physical adsorption) attachment. In one example of non-covalent attachment, a block copolymer is adsorbed onto a substrate, with one chain of the copolymer interacting strongly with the surface and the other chains forming the brushes. For example, a first polymer chain of the copolymer may be compatible with the device surface (e.g., a polymer surface formed from the same polymer or a compatible polymer) such that it becomes adsorbed to the surface. A second polymer chain of the copolymer may be selected to provide biocompatibility, whereas a third chain of the copolymer may be selected to provide reduced adhesion. For example, if the second chain is hydrophilic and biocompatible, the third chain may be hydrophobic and have reduced adhesion to other surfaces, and vice versa.

While physical adsorption is relatively simple to carry out, covalent techniques may be preferred in some embodiments, due to the stability and enhanced control over the polymer chain density which may be afforded by such techniques. Covalent attachment of polymers to form polymer brushes is commonly achieved by "grafting to" and "grafting from" techniques. "Grafting to" techniques involve tethering preformed end-functionalized polymer chains to a suitable substrate under appropriate conditions. "Grafting from" techniques, on the other hand, involve covalently immobilizing initiators on the substrate surface, followed by surface initiated polymerization to generate the polymer brushes.

Each of these techniques involves the attachment of a species (e.g., a polymer or an initiator) to a surface, which may be carried out using a number of techniques that are known in the art.

For instance, covalent coupling of species to a substrate surface, each having reactive functional groups, may be carried out by direct reaction between the functional groups, or through the use of linking/coupling agents that contain reactive moieties capable of reaction with such functional groups. Specific examples of known linking agents include glutaraldehyde, diisocyanates, diiosothiocyanates, bis(hydroxysuccinimide)esters, maleimidehydroxysuccinimide esters, carbodiimides, N,N'-carbonyldiimidazole imidoesters, and difluorobenzene derivatives, among others. One ordinarily skilled in the art will recognize that any number of other coupling agents may be used depending on the functional groups present. Further information on covalent coupling may be found, for example, in U.S. Pub. No. 2005/0002865, which is incorporated by reference.

For many substrates, including polymer substrates, surface functional groups may be introduced by treating the substrate with a reactive plasma. For example, gas discharge techniques, in which surface modification is achieved by exposing the surface to a partially ionized gas (i.e., to a plasma). Because the plasma phase consists of a wide spectrum of reactive species (electrons, ions, etc.) these techniques have been used widely for functionalization of polymer surfaces. Two types of processes are frequently described, depending on the operating pressure: corona discharge techniques (which are conducted at atmospheric pressure) and glow discharge techniques (which are conducted at reduced pressure). Glow discharge techniques may be preferred over corona discharge techniques in certain embodiments, because the shape of the object to be treated is of minor importance during glow discharge processes. Moreover, glow discharge techniques are usually either operated in an etching or in a depositing mode, depending on the gas used, whereas corona discharge techniques are usually operated in an etching mode. A commonly employed glow discharge technique is radio-frequency glow discharge (RFGD).

Plasma treatment processes may be used to etch, crosslink and/or functionalize polymer surfaces, with these processes typically occurring simultaneously at a polymer surface that is exposed to a discharge of a non-polymerizable gas. The gas that is used primarily determines which of these processes is dominant. As seen from the table below (adapted from "Functionalization of Polymer Surfaces," Europlasma Technical Paper, May 08, 2004), depending on the gas that is used, a variety of various functional groups may be generated on a given polymer.

| Plasma treatment gas | Substrate* | Functional groups |
|---|---|---|
| Ar | SR | $C{=}O$ |
| $O_2$, Ar | PP, PS | $C{-}O, C{=}O$ |
| $O_2$ | PE | $C{-}O\,(C{-}O{-}C), C{=}O, C(O){-}O$ |
| CO, $CO_2$ | PE | $-OH, C{=}O, C(O)OH$ |
| $CO_2$ | PP | $C{=}O, C(O){-}O, C{=}C$ |
| $CO_2$ | SR | $C{=}O, C{=}C$ |
| $SO_2$ | PU | $-SO_2, -SO_3$ |
| $H_2O$ | PE, PP, PS, PET, PMMA | $-OH$ |

-continued

| Plasma treatment gas | Substrate* | Functional groups |
|---|---|---|
| $N_2$ | PE | C—N, C=N |
| $NH_3$ | SR | —C(O)—NH— |
| $NH_3$ | Kevlar | C—$NH_2$ |
| $N_2O$/Ar | PET | C=O (aldehyde) |

*where SR is silicone rubber or poly(dimethyl siloxane), PS is polystyrene, PE is polyethylene, PP is polypropylene, PU is polyurethane, PET is poly(ethylene terepthalate), and PMMA is poly(methyl methacrylate).

Functional-group-containing surfaces may also be obtained for polymeric and non-polymeric substrates using plasma polymerization processes in which so-called "monomers" are employed that contain functional groups. By using a second feed gas (commonly a non-polymerizable gas) in combination with the unsaturated monomer, it is possible to incorporate this second species in the plasma deposited layer as well. Examples of gases that may be used include, allylamine, pyridine, nitroethane, ethylene oxide, allylalcohol, ethylene glycol monomethyl ether, acrylic acid, n-vinyl pyrrolidone, acetylene/$H_2O$, acetylene/CO, acetylene/$N_2$, acetylene/CO/$H_2O$, acetylene/$N_2$/$H_2O$, ethylene/$N_2$, allylamine/$NH_3$, acetylene/$SO_2$, ethylene/$SO_2$, and acrylic acid/$CO_2$, among others. Examples of functional groups that have been reportedly formed using these methods include amine, hydroxyl and carboxylate groups, among numerous others.

Further information concerning plasma functionalization may be found, for example, in "Functionalization of Polymer Surfaces," Europlasma Technical Paper, May 08, 2004 and in U.S. Patent Application Publication No. 2003/0236323.

For conductive substrates, electrochemical processes may be employed for attachment of polymers or initiators. In this regard, technology for linking an initiator to an electrically conductive surface, including metallic substrate materials such as those discussed above (e.g., stainless steel, nitinol, etc.), is disclosed by Claes et al., "Polymer Coating of Steel by a Combination of Electrografting and Atom-Transfer Radical Polymerization," Macromolecules, Web release No. 0217130, published Jul. 19, 2003 and in Ser. No. 10/894,391, filed Jul. 19, 2004 and entitled "Medical Devices Having Conductive Substrate And Covalently Bonded Coating Layer," the contents of which are hereby incorporated by reference in their entirety. In general, the initiator will have at least one functionality that is conducive to electrografting and at least one functionality that is able to initiate free radical polymerization (e.g., an activated halide functionality, which is able to initiate ATRP polymerization of, for example, vinyl monomers). One specific example of such a species is 2-chloropropionate ethyl acrylate (cPEA).

As noted above, in the "grafting from" process once an initiator is attached to the surface, a polymerization reaction is then conducted to create a surface bound polymer. Various polymerization reactions may be employed, including various condensation, anionic, cationic and radical polymerization methods. These and other methods may be used to polymerize a host of monomers and monomer combinations.

Specific examples of radical polymerization processes are controlled/"living" radical polymerizations such as metal-catalyzed atom transfer radical polymerization (ATRP), stable free-radical polymerization (SFRP), nitroxide-mediated processes (NMP), and degenerative transfer (e.g., reversible addition-fragmentation chain transfer (RAFT)) processes, among others. The advantages of using a "living" free radical system for polymer brush creation include control over the brush thickness via control of molecular weight and narrow polydispersities, and the ability to prepare block copolymers by the sequential activation of a dormant chain end in the presence of different monomers. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," Chem. Mater., 13:3436-3448 (2001), the contents of which are incorporated by reference in its entirety.

A few specific examples of techniques which have been used to produce brush polymers are described below.

One example of a "grafting to" techniques is described in D. Usov et al., "Mixed Polymer Brushes with Thermal Response Amplified by Roughness," Polymeric Materials: Science & Engineering 2004, 90, 622-623, in which μm-scale surface roughness was created on a semicrystalline PTFE substrate via etching with oxygen plasma. Both etched and non-etched PTFE were then activated with ammonia plasma. The following polymers were covalently attached to the aminogroups on the PTFE substrates, via their end carboxylic groups,: α,ω-dicarboxy-terminated poly(styrene-co-2,3,4,5,6-pentafluorostyrene) (PSF), α,ω-dicarboxy-terminated poly(methylacrylate-co-1,1,1,3,3,3-hexafluoroisopropyl methacrylate) (PHFA), and carboxy terminated poly(N-isopropyl acrylamide) (PNiPAAm). The polymer films were cast onto the activated substrates from a 1% solution in THF. The first (hydrophobic) polymer cast (i.e., PSF or PHFA) was grafted at 170° C. for 50 min in vacuum. After removing the non-grafted polymer, the second (hydrophilic) polymer (i.e., PNiPAAm) was cast grafted under the same conditions over 16 hours. The non-grafted polymer was again removed. Switching ability of the synthesized mixed polymer brushes upon exposure to selective solvents was observed (toluene is selective for PSF and PHFA, whereas ethanol is selective for PNiPAAm), as was thermally induced switching.

An example of a "grafting from" technique is described in M. Motornov et al., "Mixed Polymer Brushes on Polyamide Substrates," Polymeric Materials: Science & Engineering 2004, 88, 264-265. In this technique, polyamide (PA) samples were first treated with $NH_3$ plasma. An azo-initiator, 4,4'-azobis(4-cianopentanoic acid), was then covalently grafted to the plasma modified substrate, via the reaction of the aminogroups on the substrate with the hydroxy-groups on the initiator. Grafting of the polystyrene chains was performed by in situ radical polymerization, which was initiated by thermal decomposition of the azo-initiator. After washing, the residual azo-initiator was used to carry out the graft polymerization of 2-vinylpyridine. A pronounced switching effect upon exposure to toluene and ethanol was observed.

Igor Luzinov et al., National Textile Center Annual Report: November 2003 describe forming a mixed polymer brush on a poly(glycidylmethacrylate) (PGMA) substrate using a combination of the "grafting to" and "grafting from" techniques. Specifically, bromoacetic acid (BAA) molecules were attached to the PGMA surface from the gaseous phase, whereupon the reaction between the epoxy groups and carboxyl functionalities of the halogen acid led to 2-bromoisobutyric esters derivatives of the PGMA, which were then available to act as an ATRP initiator. Next, the synthesis of a poly(t-butyl acrylate) brush was carried out by melt grafting. The PTBA melt grafting "buried" the ATRP initiator under the polymer brush, which had a thickness of 12-20 nm. To complete the fabrication of the mixed brush, ATRP of styrene was carried out, initiated by the ATRP initiator. Hydrolysis of PTBA to polyacrylic acid (PAA) yielded polymer layers having hydrophobic/hydrophilic properties. The brushes changed their surface morphology, when they were exposed to solvent with different polarity. See also V. Klep et al., "Mixed Polymer Layers by 'Grafting to'/'Grafting form' Combination," *Polymeric Materials: Science & Engineering* 2003, 89, 248, in which a similar procedure was carrier out using 2-bromoisobutyric acid as initiator.

Luzinov et al. also describe a technique whereby Y-shaped block copolymers, which contained two incompatible polystyrene (PS) and polyacrylic acid (PAA) arms and an aromatic functional stem having a reactive carboxylate group, were grafted to the substrate surface. It was observed that these arms are capable of local reversible rearrangements leading to a reversible surface structural reorganization in different solvents.

Analogously, switchable diblock and triblock polymers may be grafted to substrates using "grafting to" methods, "grafting from" methods, and combinations of the same. For an example of a diblock copolymer exhibiting switchable behavior see, e.g., S A Prokhorova, et al., "Can polymer brushes induce motion of nano-objects?" 2003 Nanotechnology 14 1098-1108, in which poly(methyl methacrylate-b-glycidyl methacrylate) diblock-copolymer brushes are synthesized by "grafting from" a covalently attached 2-bromoisobutyrate initiator on the surface of a silicon wafer. See also U.S. Pat. Appln. 2003/0219535 in which nitroxide mediated free radical polymerization of vaporized vinyl monomers, including acrylic acid (AAc), styrene (St), N-2-(hydroxypropyl) methacrylamide (HPMA) and N-isopropyl acrylamide (NIPAAm), on silicon wafers is demonstrated. A tri-block copolymer of poly(AAc)-poly(St)-poly(HPMA) is synthesized.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An internal medical device comprising (a) substrate having a surface region, (b) a polymer brush, and (c) a therapeutic agent disposed within or beneath said polymer brush, wherein said polymer brush comprises a block copolymer that comprises (i) a hydrophobic polymer chain selected from low glass transition temperature polyalkylene chains, low glass transition temperature poly(halogenated alkylene) chains, low glass transition temperature polysiloxane chains, low glass transition temperature polyacrylate chains and low glass transition temperature polymethacrylate chains and (ii) a low glass transition temperature polyethylene oxide hydrophilic polymer chain, wherein said polymer brush is covalently attached to said surface region, wherein said surface region has a hydrophobic surface, and wherein upon exposure of said surface region to an aqueous environment the polymer brush reorients to form a hydrophilic surface.

2. The internal medical device of claim 1, wherein said block copolymer is selected from the following: a diblock copolymer, a triblock copolymer and a pentablock copolymer.

3. The internal medical device of claim 1, wherein said hydrophobic polymer chains are selected from homopolymer chains, random copolymer chains and periodic copolymer chains.

4. The internal medical device of claim 1, wherein said medical device is a stent.

5. The internal medical device of claim 1, wherein said polymer brush covers the entire surface of said medical device.

6. The internal medical device of claim 1, wherein said polymer brush covers a portion of the surface of said medical device.

7. The internal medical device of claim 1, wherein the hydrophobic polymer chains are oriented at the surface by contacting said polymer brush with a hydrophobic solvent.

8. The internal medical device of claim 1, wherein said therapeutic agent is compatible with said hydrophobic polymer chains.

9. The internal medical device of claim 1, wherein said therapeutic agent is compatible with said hydrophilic polymer chains.

10. The internal medical device of claim 1, wherein said surface region is a polymeric surface region.

11. The internal medical device of claim 1, wherein said therapeutic agent is selected from an anti-restenotic agent, an anti-thrombotic agent, an endothelial growth promoting agent and combinations thereof.

12. The internal medical device of claim 1, further comprising a plurality of therapeutic agents disposed within or beneath said polymer brush.

13. A treatment method comprising implanting or inserting the internal medical device of claim 1 into a patient, wherein the hydrophobic polymer chains are oriented at the surface of said device at the time of implantation or insertion, and wherein after implantation or insertion of said device into a patient the polymer brush reorganizes such that the hydrophilic polymer chains become oriented at the surface.

14. The internal medical device of claim 1, wherein said therapeutic agent is compatible with said hydrophobic polymer chains and said hydrophilic polymer chains.

15. The internal medical device of claim 1, wherein said therapeutic agent is incompatible with said hydrophobic polymer chains and said hydrophilic polymer chains.

16. The internal medical device of claim 1, wherein said hydrophobic polymer chain is selected from low glass transition temperature polyacrylate chains and low glass transition temperature polymethacrylate chains.

17. The internal medical device of claim 1, wherein said covalently attached block copolymer has a configuration selected from $CB_LL_L$ and $B_LCL_L$, where C represents a covalent linking entity for linkage to the surface of the substrate, $B_L$ represents said hydrophobic low $T_g$ chain and $L_L$ represents said hydrophilic low $T_g$ chain.

18. The internal medical device of claim 1, wherein said covalently attached block copolymer has a $CL_LB_L$ configuration, where C represents a covalent linking entity for linkage to the surface of the substrate, $B_L$ represents said hydrophobic low $T_g$ chain and $L_L$ represents said hydrophilic low $T_g$ chain.

* * * * *